United States Patent [19]

Hajko et al.

[11] Patent Number: 5,712,130
[45] Date of Patent: Jan. 27, 1998

[54] PROCESS FOR THE ISOLATION OF LOVASTATIN

[75] Inventors: Pavica Hajko; Tanja Vesel; Ivan Radež ; Miroslav Pokorny, all of Novo mesto, Slovenia

[73] Assignee: KRKA tovarna zdravil, p.o, Novo mesto, Slovenia

[21] Appl. No.: 591,669

[22] PCT Filed: Jun. 8, 1994

[86] PCT No.: PCT/SI94/00010

§ 371 Date: Jun. 17, 1996

§ 102(e) Date: Jun. 17, 1996

[87] PCT Pub. No.: WO94/29292

PCT Pub. Date: Dec. 22, 1994

[30] Foreign Application Priority Data

Jun. 8, 1993 [SI] Slovenia .................. 9300303

[51] Int. Cl.$^6$ .................. C12P 17/02; C12P 17/06; C12P 17/00

[52] U.S. Cl. .................. 435/123; 435/117; 435/125

[58] Field of Search .................. 435/117, 123, 435/125

[56] References Cited

U.S. PATENT DOCUMENTS 4,231,938 11/1980 Monaghan et al. .................. 549/292
5,156,960 10/1992 Jekkel née Bokány et al. ...... 435/71.1
5,403,728 4/1995 Jekkel et al. .................. 435/125

FOREIGN PATENT DOCUMENTS 9410328 11/1994 WIPO .

*Primary Examiner*—John W. Rollins
*Assistant Examiner*—Christopher R. Tate
*Attorney, Agent, or Firm*—Pollock, Vande Sande & Priddy

[57] ABSTRACT

There is disclosed a process for the isolation of the hypolipaemic active substance lovastatin from a sample, e.g. fermentation broth, mycelium or filtrate of *Aspergillus terreus* (ATCC 20542) or *Aspergillus oryzae* (ATCC 74135) by extraction with butyl acetate. Simultaneously with the concentration of the extract, lactonisation takes place. There follows a direct crystallization of lovastatin in the lactone form from butyl acetate.

5 Claims, 4 Drawing Sheets

PROCESS FOR THE ISOLATION OF LOVASTATIN

TECHNICAL FIELD

The invention belongs to the field of biotechnology and relates to a process for the isolation of the hypolipaemic active substance lovastatin from a fermentation broth. Lovastatin is produced as a secondary metabolite of the fungus *Aspergillus terreus* (U.S. Pat. No. 4,231,938) deposited in American Type Culture Collection under Nos. ATCC 20541, ATCC 20542, and *Monascus ruber* deposited in Fermentation Research Institute Agency of Industrial Science and Technology, Ministry of International Trade and Industry, Japan (DE 30 06 216 A1) under No. Ferm 4822. Other kinds of microorganisms producing lovastatin are known as well, e.g. a mutant of the microorganism *Aspergillus terreus* and *Aspergillus oryzae* marked ATCC 74135.

Lovastatin is chemically 1',2',6',7',8a'-hexahydro-3,5-dihydroxy-2',6'-dimethyl-8'-2"-methyl-1"-oxobutoxy)-1-naphtalene heptanoic acid-5-lactone (Stubbs et al., 1986) of the formula. (EP 0 033 537 A1)

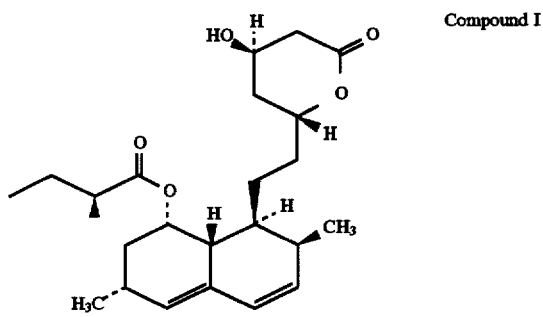

Compound I

An active form of lovastatin is also an acid, which is chemically 1,2,6,8,8a-hexahydro-β,δ-dihydroxy-1-naphtalene heptanoic acid (Alberts et al., 1980) of the formula (EP 0 022 478 A1)

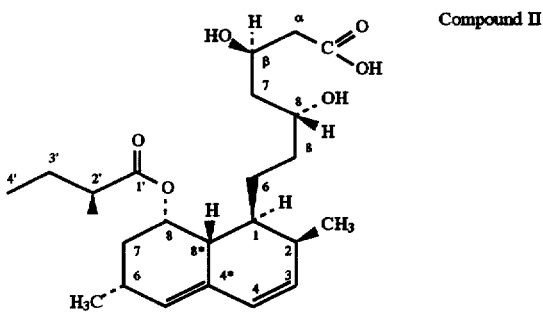

Compound II

The lactone form of lovastatin is used as an agent for reducing cholesterol level in blood (Scott M. G. and Vega G. L., 1985). It inhibits the biosynthesis of mevalonic acid by inhibition of 3-hydroxy-3-methylglutaryl A reductase coenzyme (HMG-CoA reductase, E.C. 1.1.1.34) (Zubay et al., 1984).

PRIOR ART

After the completed fermentation, lovastatin is present in the broth in the lactone form (compound I) and in the acid form (compound II). In the isolation process as disclosed in EP 0 033 536 A2, lovastatin is extracted from the broth with ethyl acetate. The extract is concentrated by vacuum distillation. Since lovastatin is present in the lactone form as well as in the acid form and only the lactone is of commercial interest, the acid form should be converted into the lactone. The lactonisation is carried out by the reflux of the concentrate in toluene at 106° C. for 2 hours. After the lactonisation is complete, the solution is concentrated to a small volume. A pure substance is obtained by means of purifying the concentrate on columns packed with silica gel, in the presence of solvents such as ethyl acetate or n-hexane. The collected fractions are again concentrated in vacuo and then pure lovastatin crystallizes in the lactone form.

Due to the sophisticated multi-step procedure and vigorous conditions applied during the isolation, the yields of lovastatin are generally low. Different solvents, which in part exhibit toxicity, are used such as benzene, toluene, acetonitrile or ethyl acetate. Hence working with these solvents endangers the health of the persons involved and poses a problem with respect to the environment.

DESCRIPTION OF THE INVENTION

An object of the present invention was to overcome the above deficiencies of the state of the art and to provide a process for isolating lovastatin in an efficient and economic way. In addition, attention should be paid to health aspects of the workers involved in the isolation and to the environment.

As a result of extensive search leading to the present invention, the present inventors have found that lovastatin may be easily isolated by extracting lovastatin from a sample with butyl acetate, concentrating the solution and carrying out a crystallization.

In a preferred embodiment the concentration of the solution is carried out under reduced pressure. In a further preferred embodiment concentration is carried out at a temperature above 40° C. with or without reduced pressure.

In yet another preferred embodiment the sample of lovastatin is derived from microorganisms, preferably a fungus capable of producing lovastatin. In this case the sample may be the fermentation broth in which the microorganism or the fungus, respectively, has been grown, the mycelium of the fungus or the filtrate.

The fungus to be used is not limited and any fungus capable of producing lovastatin may be utilized, with those belonging to the genus Aspergillus, preferably *Aspergillus oryzae* or *Aspergillus terreus*, being preferred.

In yet another preferred embodiment the fungus is *Aspergillus terreus* (ATCC 20542) or *Apergillus oryzae* (ATCC 74135).

According to the process of the present invention lovastatin may be obtained exclusively in the lactone form. It has surprisingly been found that the solvent utilized, i.e. butyl acetate, provides features enabling to achieve this goal. Namely, in the lactonisation process water is released and should be removed from the reaction medium. Since butyl acetate has a higher boiling point and does not substantially form azeotropic mixtures with water under the given conditions, essentially all water formed during the lactonisation process may be removed.

By the process according to the present invention it has become possible to substantially shorten the time for isolating lovastatin. Since butyl acetate may be used to extract lovastatin from a sample and at the same time may be utilized for performing the lactonisation, the toxic effects of other solvents may be obviated. The process may be industrially reproduced with the final yields of about 60%, irrespective of lovastatin being produced by microorganisms intracellularly or extracelullarly, in the lactone form or in the acid form.

Figure 1:
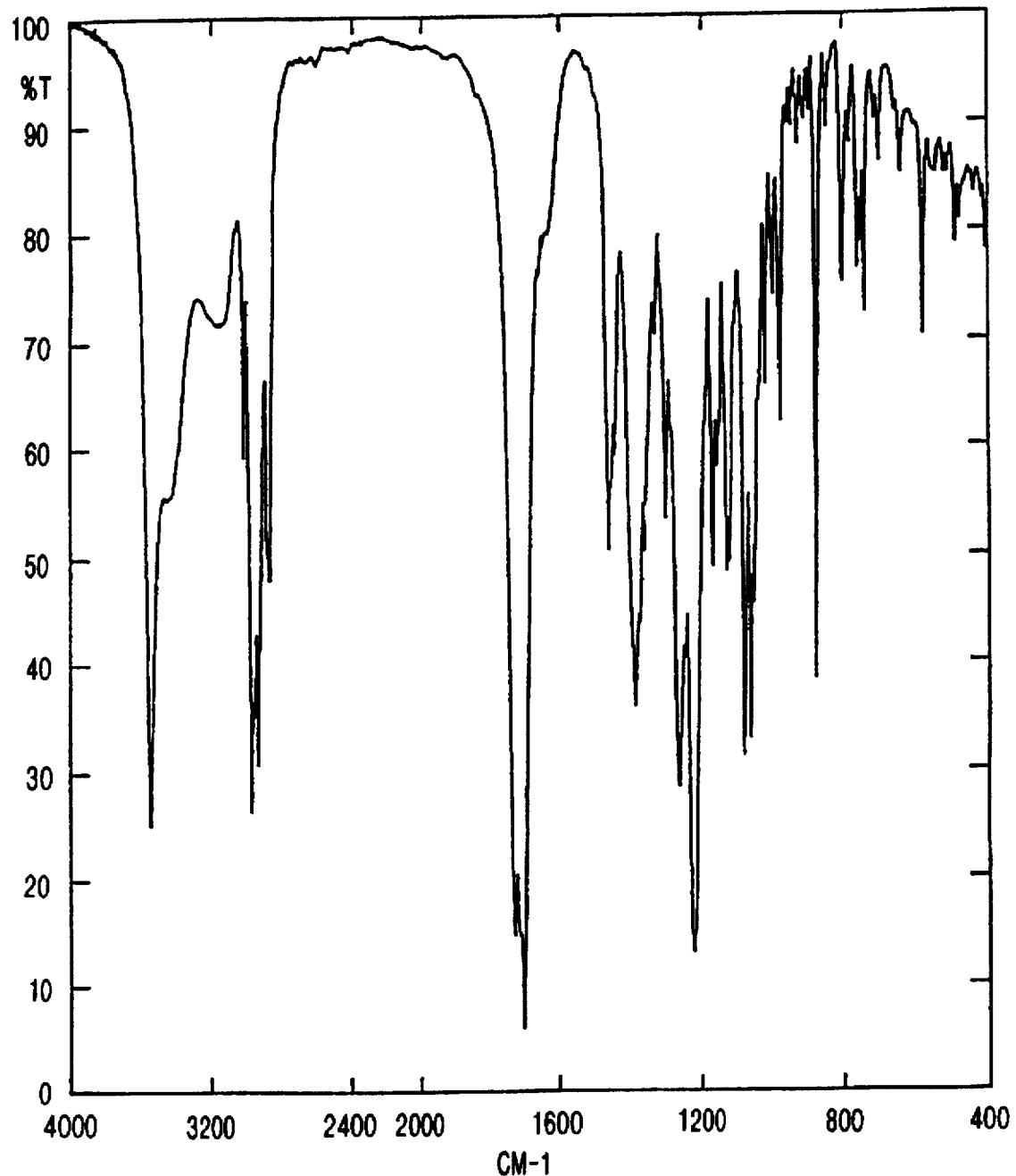
FIG. 1 represents the results of IR spectroscopy confirming the structure of the substance isolated according to the present invention.
Figure 2:
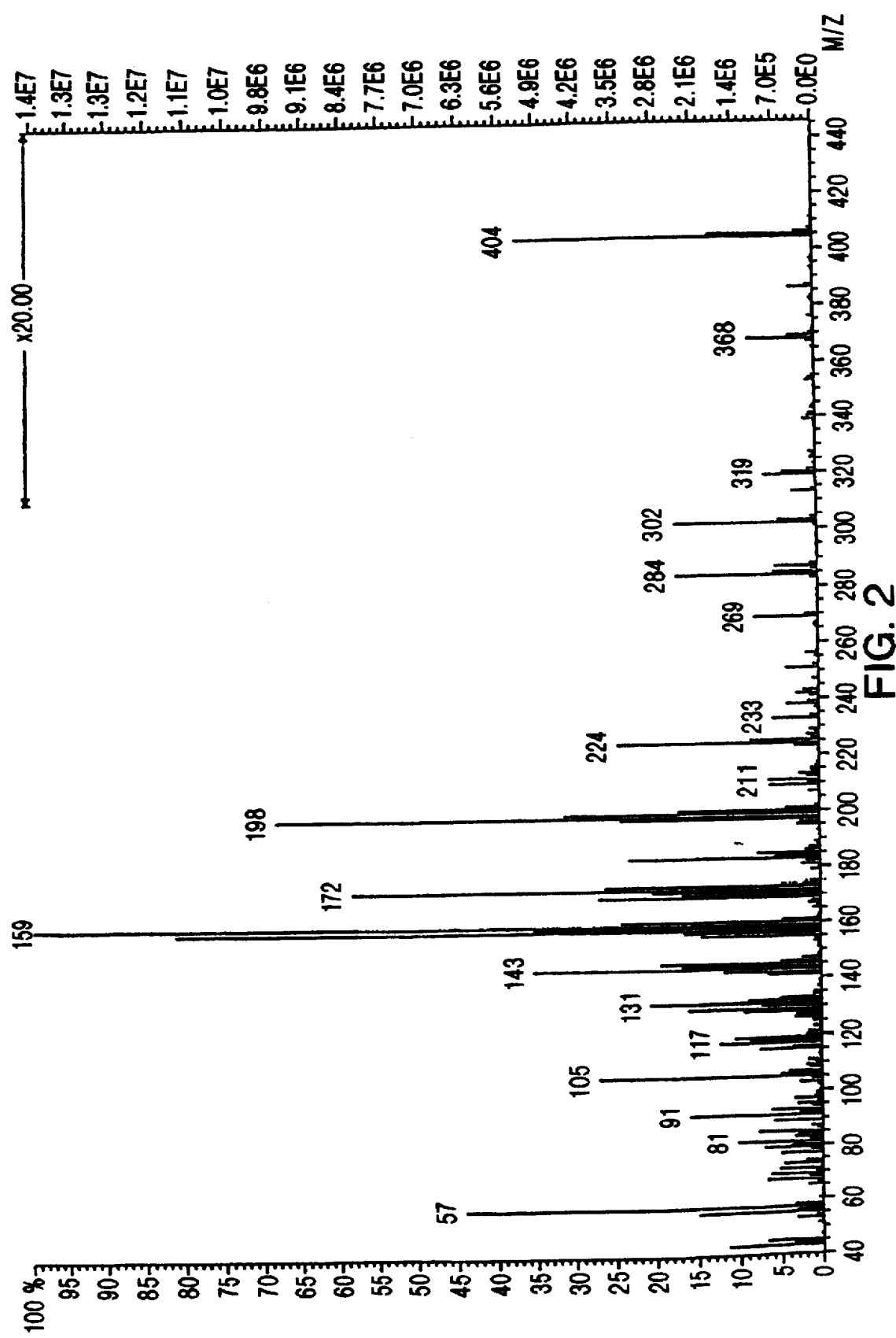
FIG. 2 represents the results of mass spectroscopy confirming the structure of the substance isolated according to the present invention.
Figure 3:
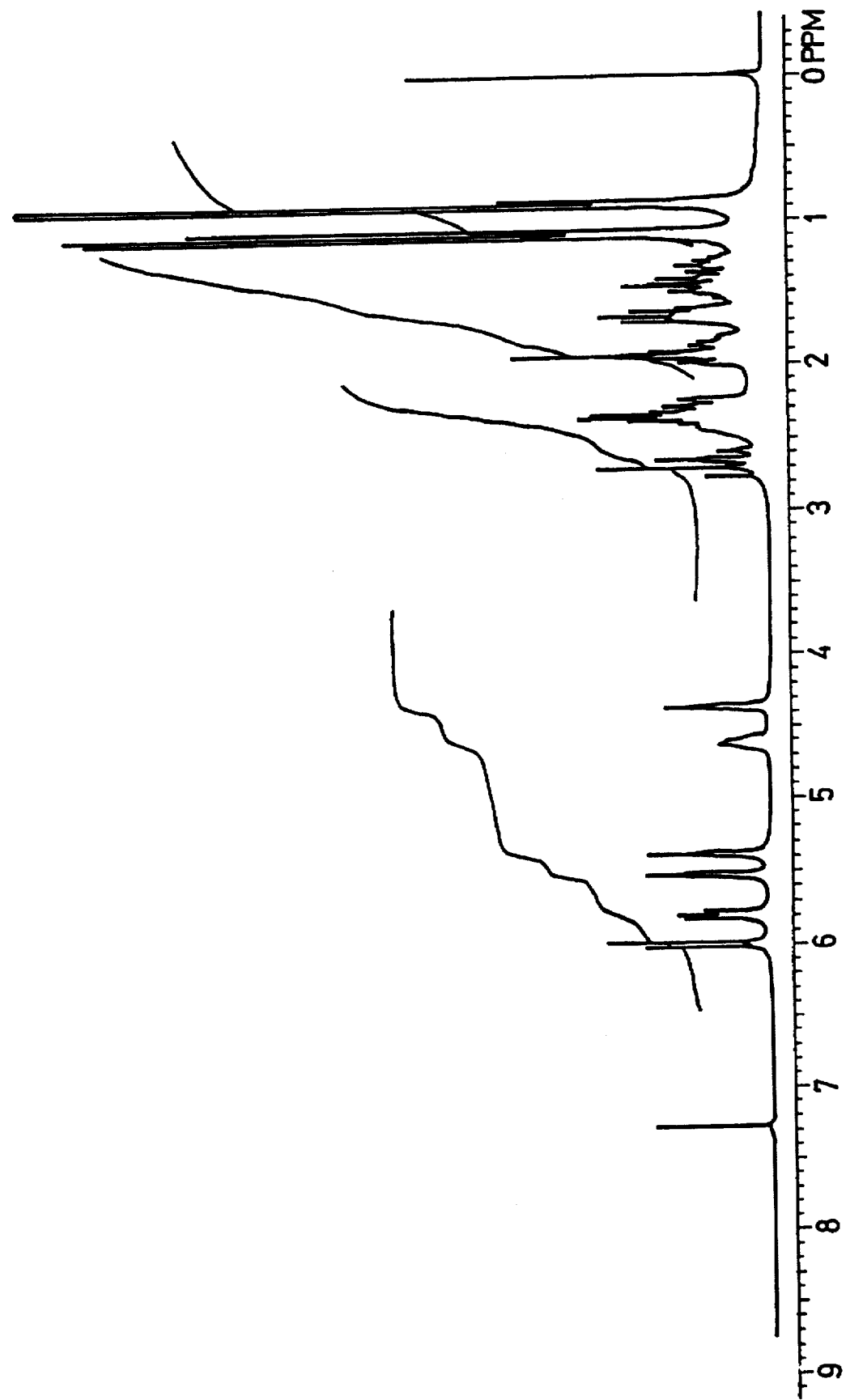
FIG. 3 represents the results of NMR confirming the structure of the substance isolated according to the present invention.
Figure 4:
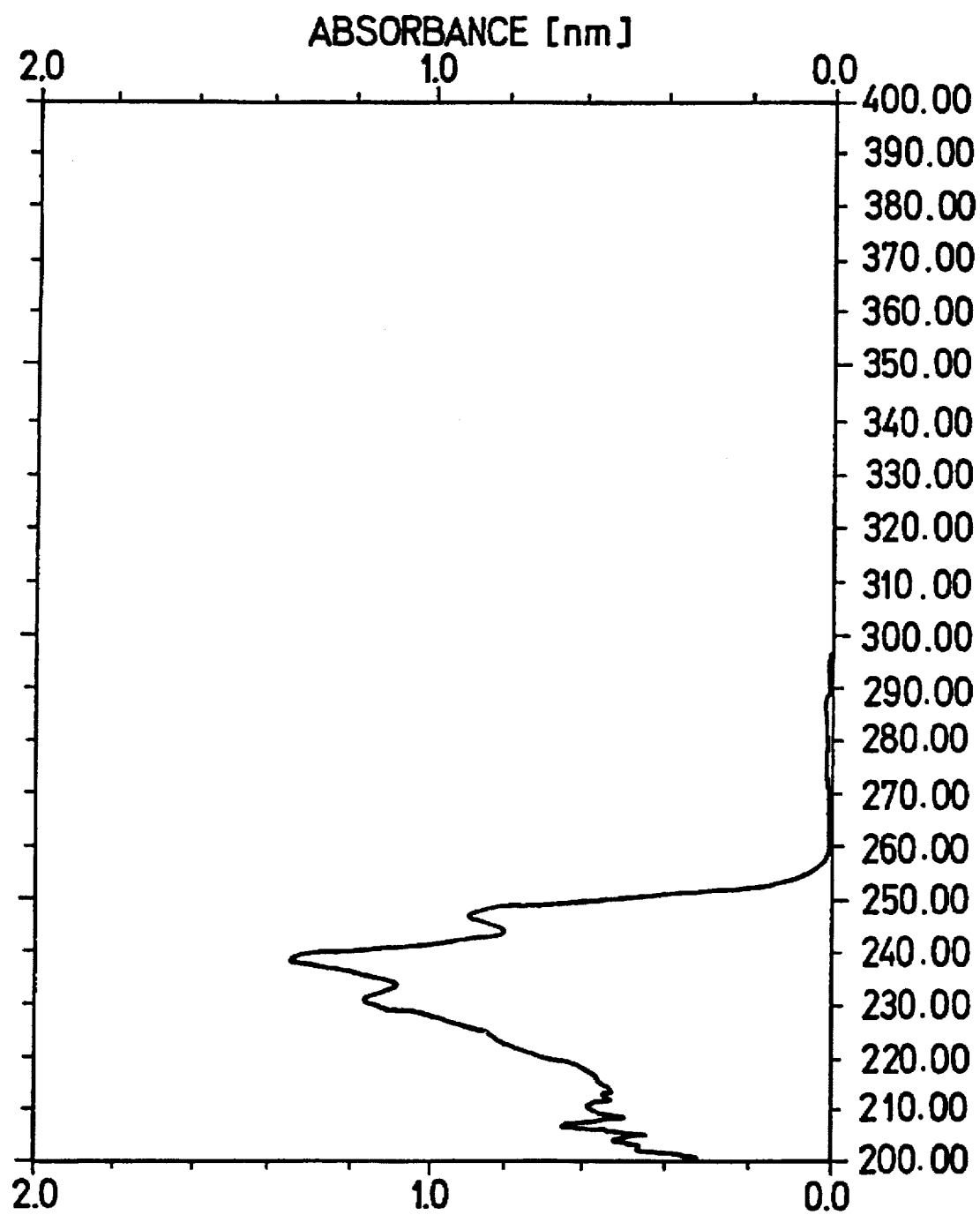
FIG. 4 represents the results of UV spectroscopy confirming the structure of the substance isolated according to the present invention.

The isolated substance is the same as the substance isolated according to Prior Art processes. The structure was confirmed by IR spectroscopy (FIG. 1), mass spectroscopy (FIG. 2), NMR (FIG. 3) and UV spectroscopy (FIG. 4).

The invention is illustrated by the following non-limiting Examples.

EXAMPLE 1

Fermentation broth (1000 ml) obtained by the fermentation of *Aspergillus terreus* (ATCC 20542) or *Aspergillus oryzae* (ATCC 74135) and having a pH value of 4.8, an age of 120 hours and a lovastatin content of 300 µg/ml (lactone+acid) was acidified with HCl (36%) to a pH of 3–5. The fermentation broth was then cooled below 20° C., butyl acetate (500 ml) was added and it was extracted for 4 hours at this temperature. After the extraction was complete, it was centrifuged and the aqueous and organic phases were separated. The mycelium and the aqueous phase were discarded and the organic phase was further treated. It was concentrated by vacuum distillation at a temperature above 40° C. to a volume of 50 ml. Simultaneously with the concentration, the lactonisation process took place as well. The concentrate was then cooled to a temperature below 20° C. and left to stand a few hours so that lovastatin crystallized. The obtained crude product was recrystallized. Lovastatin (170 mg) in the lactone form having a purity above 90% was obtained.

EXAMPLE 2

Fermentation broth (1000 ml) obtained by the fermentation of *Aspergillus terreus* (ATCC 20542) or *Aspergillus oryzae* (ATCC 74135) and having a pH value of 4.73, an age of 120 hours and a lovastatin content of 190 µg/ml (lactone+acid) in the filtrate and 15 µg/ml in the mycelium was acidified with HCl (36%) to a pH of 3–5. The broth was filtered over Oliver filter. The mycelium was discarded, the filtrate was cooled to a temperature below 20° C. and half the volume of butyl acetate was added. It was extracted for 1 hour. Then it was proceeded as in Example 1. Lovastatin (79 mg) in the lactone form having a purity above 90% was obtained.

EXAMPLE 3

Fermentation broth (1000 ml) obtained by the fermentation of *Aspergillus terreus* (ATCC 20542) or *Aspergillus oryzae* (ATCC 74135) and having a pH value value of 4.78, an age of 120 hours and a lovastatin content of 5 µg/ml (lactone+acid) in the filtrate and 300 µg/ml in the mycelium was acidified with HCl (36%) to a pH of 3–5 and centrifuged. The filtrate was discarded, a 4-fold volume of butyl acetate was added to the mycelium and it was cooled below 20° C. It was extracted for 4 hours. The extraction was followed by centrifuging. The mycelium was discarded and the filtrate treated as in Example 1. Lovastatin (90 mg) in the lactone form having a purity above 90% was obtained.

We claim:

1. A process for isolating lovastatin from a fermentation broth, mycelium or filtrate of a microorganism which produces lovastatin which comprises extracting lovastatin with butyl acetate to thereby obtain a solution of lovastatin in butyl acetate; concentrating said solution of lovastatin in butyl acetate under reduced pressure and at a temperature above 40° C.; and permitting the lovastatin to crystallize.

2. A process according to claim 1, wherein said microorganism for producing lovastatin is a fungus.

3. A process according to claim 2, wherein said fungus belongs to the genus Aspergillus.

4. A process according to claim 3, wherein said fungus belongs to the species *Aspergillus terreus* or *Aspergillus oryzae*.

5. A process according to claim 4 wherein said fungus is *Aspergillus terreus* ATCC 20542 or *Aspergillus oryzae* ATCC 74135.

* * * * *